United States Patent [19]

Nestor, Jr. et al.

[11] Patent Number: 4,686,283
[45] Date of Patent: Aug. 11, 1987

[54] ANALOGS OF TRANSFORMING AND EPIDERMAL GROWTH FACTOR FRAGMENTS FOR THERAPY AND DIAGNOSIS

[75] Inventors: John J. Nestor, Jr., San Jose; Alain B. Schreiber, Sunnyvale, both of Calif.

[73] Assignee: Syntex (U.S.A.) Inc., Palo Alto, Calif.

[21] Appl. No.: 723,785

[22] Filed: Apr. 16, 1985

[51] Int. Cl.[4] ............................ C07K 7/06; C07K 7/08
[52] U.S. Cl. ....................................... 530/327; 530/328
[58] Field of Search ......................... 530/326, 327, 328

[56] References Cited

FOREIGN PATENT DOCUMENTS 0132021 1/1985 European Pat. Off. .

OTHER PUBLICATIONS

Proc. of the Natl. Acad. of Science (1985), vol. 82, No. 16, 5300–5304.
Biochem. and Biophys. Res. Commun., vol. 729, No. 1, (1985) 226–232.
The Journal of Biological Chemistry (1985), vol. 260, No. 11, pp. 7059–7066.
Proc. of the Natl. Acad. of Sciences (1985), vol. 82, No. 2, 356–360.

*Primary Examiner*—Delbert R. Phillips
*Attorney, Agent, or Firm*—Liza K. Toth; Tom M. Moran

[57] ABSTRACT

Polypeptides analogs of fragments of TGFα and EGF are useful as therapeutic and diagnostic agents.

33 Claims, No Drawings

1

ANALOGS OF TRANSFORMING AND EPIDERMAL GROWTH FACTOR FRAGMENTS FOR THERAPY AND DIAGNOSIS

BACKGROUND OF THE INVENTION

1. Field of the Invention

This invention relates to novel polypeptides which are modifications of fragments of transforming growth factors (TGF). Certain of these compounds are immunogens and thus raise antibodies which are useful for detecting the presence of TGFα in the samples of fluids. These antibodies can be combined with a conjugate to prepare a diagnostic kit. Certain of the compounds of this invention are analogs of TGFα fragments or the homologous epidermal growth factor (EGF) fragments which are antagonists of TGFα and are useful for blocking the cell proliferation effects of TGFα in a mammal.

2. Related Art

Transforming growth factors (TGF) comprise a family of hormone-like polypeptides which confer the transformed or tumor phenotype on normal cells. Such transformed cells are stimulated to lose anchorage dependence and contact inhibition of growth. The human TGFα molecule is structurally related to human epidermal growth factor (EGF) and binds to EGF receptors. TGFα has been detected at elevated levels in the urine of patients with several classes of solid tumors (e.g. bronchogenic carcinoma, breast and bowel carcinoma, and the like). The development of an assay and diagnostic kit capable of detecting and quantitating the TGFα molecule without excess cross-reactivity with EGF would be of great interest in diagnosing and managing many classes of solid tumors.

The most convenient and sensitive way to detect TGFα would be through the use of a specific antibody-based assay system. However, the antibodies would have to be raised against TGFα, and TGFα would have to be used as a calibration reagent to accompany the assay system. Because the purification and isolation of TGFα is difficult and expensive, the use of TGFα for these purposes is not economically feasible at the present time.

The structure of rat transforming growth factor has been reported to be Val-Val-Ser-His-Phe-Asn-Lys-Cys-Pro-Asp$^{(10)}$-Ser-His-Thr-Gln-Tyr-Cys-Phe-His-Gly-Thr$^{(20)}$-Cys-Arg-Phe-Leu-Val-Gln-Glu-Glu-Lys-Pro$^{(30)}$-Ala-Cys-Val-Cys-His-Ser-Gly-Tyr-Val-Gly$^{(40)}$-Val-Arg-Cys-Glu-His-Ala-Asp-Leu-Leu-Ala [Marquardt, et al., *Science*, 223, 1079 (1984)]. The human TGFα sequence is closely related and, in residues 34–43 differs from the rat TGF only by the replacement of the valyl residue by an alanyl residue at position 41 [Derynck, et al., *Cell*, 38, 287 (1984)]. Human EGF is reported to be a 53 residue polypeptide with the sequence of residues 34–43 being Cys-Val-Val-Gly-Tyr-Ile-Gly-Glu-Arg-Cys [Carpenter and Cohen, *Ann. Rev. Biochem.*, 48, 193–216 (1979)].

The use of a suitable polypeptide fragment, instead of the whole TGF molecule, to raise antibodies and as a calibration reagent would offer the advantages of easier synthesis and lower cost.

We have discovered that certain polypeptides, which are modified fragments of TGFα, produce specific antibodies which react with TGFα but do not cross-react with EGF, thus providing a means for a diagnostic system which is capable of detecting TGFα in the presence of EGF. We have also discovered that polypeptides, which are modified fragments of TGFα, bind to EGF receptors but do not stimulate epidermal cell growth. Thus, these compounds are competitive inhibitors of TGFα and as such are useful for blocking the cell proliferation effects of TGFα. In addition, the corresponding fragment of EGF and analogs thereof bind to the EGF receptor and also represent antagonists of EGF or TGF.

SUMMARY OF THE INVENTION

One aspect of this invention comprises a compound represented by the formula

A—B—C—               (I)

—Cys—D—E—Gly—Tyr—F—Gly—G—Arg—Cys—

—H—I—J, the reduced form of said compound, or a pharmaceutically acceptable salt of said compound, wherein A is hydrogen, acyl of one to twelve carbon atoms, benzoyl, 3-(4-hydroxyphenyl)propionyl, or 3-(3,5-diiodo-4-hydroxyphenyl)propionyl;

B is a bond or a radical of the formula

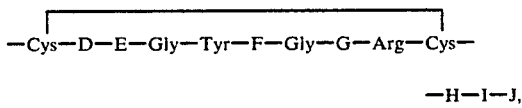

C is (Gly)$_x$ or (Ala)$_x$;

D is Val or His;

E is Ser, Ile or Val;

F is Val, Ser or Ile;

G is Val, Ala, Asp or Glu;

H is (Gly)$_y$ or (Ala)$_y$;

I is a bond or a radical represented by formula (II), but independent thereof; and J is OR$_7$ or NHR$_8$, wherein for B, C, H, I and J n is an integer of two to five;

each of x and y is independently an integer of zero to five;

R$_1$ is alkyl of one to twelve carbon carbon atoms or —NRR$_3$ wherein

R is hydrogen or lower alkyl and

R$_3$ is hydrogen, alkyl of one to twelve carbon atoms, lower fluoroalkyl, cycloalkyl, phenyl or benzyl;

R$_2$ is hydrogen, alkyl of one to twelve carbon atoms, lower fluoroalkyl, cycloalkyl, phenyl or benzyl, or R$_1$—C=NR$_2$ in formula (II) represents a radical chosen from the group

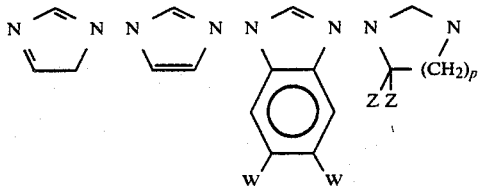

wherein
- p is an integer of one to seven; each Z is independently hydrogen, lower alkyl or cycloalkyl; and each W is independently halo or Z;
- $R_7$ is lower alkyl or hydrogen, provided that
- $R_7$ is not hydrogen when A is hydrogen, B is a bond and x is 0; and
- $R_8$ is hydrogen, lower alkyl or lower fluoroalkyl.

Another aspect of this invention comprises a complex which is the combination of the compounds of formula (I), as defined above, bound to a suitable carrier.

Another aspect of this invention comprises antibodies raised against a compound of formula (I) coupled to a suitable carrier, particularly wherein the compound is represented by formula (I), above, wherein
- A is hydrogen
- B is bond
- C is $(Gly)_x$ or $(Ala)_x$ where x is 0, 1 or 2,
- E is Ser;
- F is Val;
- G is Val or Ala;
- y is 0;
- I is a bond; and
- J is $NH_2$.

Another aspect of this invention comprises a method for blocking the cell proliferation effects of TGFα in a mammal, which method comprises administering to a mammal in need thereof a compound represented by formula (I), the reduced form of the compound or a pharmaceutically acceptable salt of the compound, particularly those wherein A, D, E, F, G, H, I and J are as defined for formula (I), above; B is a radical of formula (II); C is $(gly)_x$; and x is an integer of one to five.

Still another aspect of this invention comprises a method for determining human TGFα in a sample suspected of containing same, which method comprises
(a) contacting the suspected sample with the antibodies of this invention under binding conditions and
(b) observing the presence of binding by antibodies to the TGFα.

Still another aspect of this invention is a diagnostic kit which comprises
(a) a conjugate of (1) a label which produces a signal and (2) an antibody of this invention optionally in combination with
(b) a calibrating amount of a compound of formula (I) or that compound bound to a suitable carrier.

In yet another aspect, the present invention relates to a method for preparing compounds of the invention, which process comprises:
- removing protecting groups and, optionally, covalently bound solid support from a protected polypeptide to afford a compound of Formula (I), its reduced form or a salt thereof;
- coupling together in the required sequence two polypeptides fragments to form the desired compound of formula (I);
- converting a compound of Formula (I) to a pharmaceutically acceptable salt thereof;
- converting a salt of a compound of Formula (I) to a pharmaceutically acceptable salt;
- decomposing a salt of a compound of Formula (I) to a free polypeptide of Formula (I);
- reducing a compound of formula (I) to its reduced form.

ABBREVIATIONS AND DEFINITIONS

As set forth above, and for convenience in describing the compounds of this invention, the conventional abbreviations for the various common amino acids are used as generally accepted in the peptide art as recommended by the IUPAC-IUB Commission on Biochemical Nomenclature, *Biochemistry*, 11, 1726 (1972). These represent L-amino acids, with the exception of the achiral amino acid glycine. All peptide sequences mentioned herein are written according to the generally accepted convention whereby the N-terminal amino acid is on the left and the C-terminal amino acid is on the right.

Certain other abbreviations will be useful in describing the invention. The present invention employs replacements of naturally occuring amino acids by amino acids which do not occur in nature. These replacements will be seen for "B" and "I" in formula (I). The radicals represented by formula (II) include residues which are D- and L-amino acid residues. Commonly employed among these are the following, which designations refer to both the D- and L-isomer unless otherwise specified:

| Amino acid residue | Abbreviation |
| --- | --- |
| N,N'—guanidino-dimethyl-homoarginine | Dmh |
| N,N'—guanidino-diethyl-homoarginine | Deh |
| N,N'—guanidino-dipropyl-homoarginine | Dph |
| N,N'—guanidino-diisopropyl-homoarginine | Dih |
| N,N'—guanidino-dihexyl-homoarginine | Dhh |
| N—guanidino-isopropyl-homoarginine | Iph |
| N—guanidino-heptyl-homoarginine | Hha |
| N—guanidino-propyl-homoarginine | Prh |
| N,N'—guanidino-dicyclohexyl-homoarginine | Dch |
| N,N'—guanidino-diisopropyl-arginine | Dia |
| N,N'—guanidino-diethyl-arginine | Dea |
| N,N'—guanidino-dicyclohexyl-arginine | Dca |
| N—guanidino-(3-dimethylaminopropyl)-N'—guanidino-ethyl-homoarginine | Aph |
| N—guanidino-(3-dimethylaminopropyl)-N'—guanidino-ethyl-arginine | Apa |
| 3-(3-piperidyl)-alanine | 3-Pia |
| 3-(4-piperidyl)-alanine | 4-Pia |
| 3-(($N^\epsilon$-methyl)piperid-4-yl)-alanine | Mpa |
| 3-(($N^\epsilon$-pentyl)piperid-4-yl)-alanine | Ppa |
| 3-(($N^\epsilon$-benzyl)piperid-4-yl)-alanine | Bpa |
| N,N'—ethylene-homoarginine | Dhi |

As used herein, the term "pharmaceutically acceptable salt" refers to a salt that retains the desired biological activity of the parent compound and does not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (C) salts formed with an organic cation formed from N,N'-dibenzylethylenediamine or ethylenediamine; or (d) combinations, of (a) and (b) or (c), e.g., a zinc tannate salt and the like.

The term "lower alkyl" refers to a straight or branched chain saturated hydrocarbon radical having from 1 to 4 carbon atoms such as, for example, methyl, ethyl, n-propyl, isopropyl, n-butyl, isobutyl, sec-butyl and tert-butyl. "Alkyl of 1 to 6 carbon atoms" includes lower alkyl but in addition the hydrocarbon group may have 5 or 6 carbon atoms such as, for example, a n-pentyl, n-hexyl or other branched 5 or 6 carbon membered moiety. "Carbon atoms" refers to a straight or branched saturated hydrocarbon radical of 1 to 12 carbon atoms, and includes any alkyl radical of 1 to 6 carbon atoms along with any alkyl radical of 7–12 carbon atoms such as heptyl, octyl, nonyl, decyl, dodecyl and the like.

The term "cycloalkyl" refers to a cyclic saturated hydrocarbon group having from 3 to 6 carbon atoms, for example, cyclopropyl, cyclobutyl, cyclopentyl and cyclohexyl.

The term "lower fluoroalkyl" means an alkyl radical of 2 to 4 carbons substituted with at least one fluoro at least one carbon removed from the point of attachment. Examples include 2,2,2-trifluoroethyl, 2,2,3,3,3-pentafluoropropyl and the like.

"Acyl" denotes a straight or branched chain saturated hydrocarbon acid radical having 1 to 12 carbon atoms such as formyl, acetyl, propionyl, butyryl, octanoyl, decanoyl, dodecanoyl, and the like.

The "reduced form" of a compound of formula (I) is the compound which has no disulfide bond between the cys residues in the polypeptide chain.

DETAILED DESCRIPTION AND PRESENTLY PREFERRED EMBODIMENTS

The compounds of this invention in their broadest aspect are defined above in the "Summary of the Invention." A preferred subgroup includes the compounds of the formula

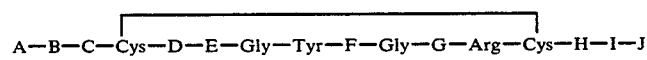

wherein
A is hydrogen;
B is a bond;
x is an integer of 0 to 2;
y is 0;
I is a bond; and
J is $NH_2$.

Of these, the compounds where C is Gly, D is His, is E is Ser, F is Val and G is Ala or Val are of particular interest, with preferred compounds being those where G is Ala and x is zero. Preferred representative compounds include the following:

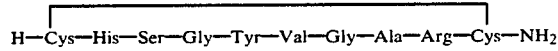

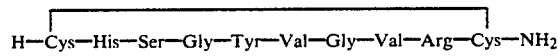

or the reduced forms thereof.

Another preferred subgroup includes the compounds of formula (I)
wherein
A is acyl of one to twelve carbon atoms, benzoyl, 3-(4-hydroxyphenyl)propionyl- or 3-(3,5-diiodo-4-hydroxyphenyl)propionyl;
B is a bond;
x is an integer of 0 to 2;
y is 0;
I is a bond; and
J is $NH_2$.

Of this subgroup, compounds of particular interest are those of formula (I) where C is Gly, D is His, E is Ser, F is Val, G is Ala or Val and x is 0; and preferrably those where A is acetyl, 3-(3,5-diiodo-4-hydroxyphenyl)propionyl or 3-(4-hydroxyphenyl)propionyl.

Still another preferred subgroup includes compounds of formula (I)
wherein
A is hydrogen or acyl of one to twelve carbon atoms;
B is the radical of formula (II) wherein $R_1$ is $NR_3R$;
C is Gly; and
x is an integer of one to five.
Of particular interest are the compounds of formula (I) wherein for formula (II)
R is hydrogen;
$R_2$ is alkyl of one to twelve carbon atoms or lower fluoroalkyl; and
$R_3$ is hydrogen or alkyl of one to twelve carbon atoms, especially the compounds wherein in formula (I)
y is an integer of 2–5;
I is a radical of formula (II) wherein
$R_1$ is $NRR_3$ and
J is $NHR_8$.

Particularly preferred are compounds of the formula

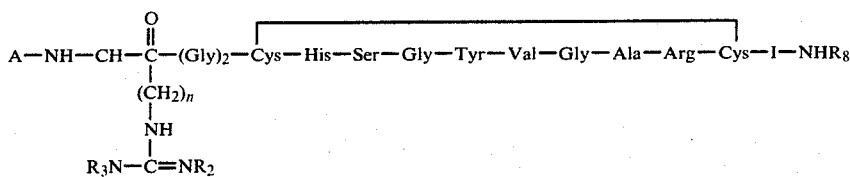

where A is Acyl of 1-12 carbon atoms and $R_8$ is H or lower alkyl.

Representative preferred compounds include

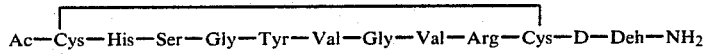

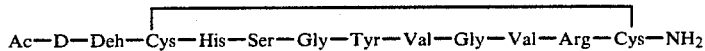

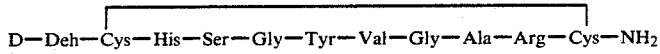

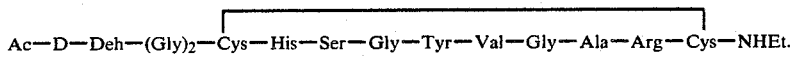

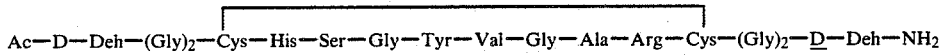

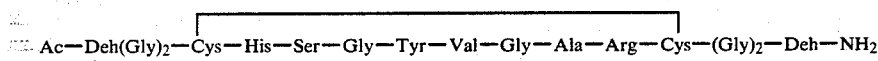

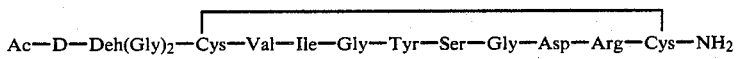

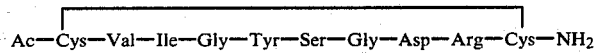

A central aspect of this invention is that the polypeptides disclosed here may be used in the diagnosis of cancer. This diagnostic capability is derived from the fact that antibodies to the compounds of formula (I) may be prepared either from the compounds themselves or the compounds bound to a suitable carrier. Such antibodies are then employed in the method or diagnostic kit of this invention in such a manner as to determine the concentration of TGFα in a specimen, the presence or absence of TGFα being predictive of the presence or absence of cancer cells in the specimen source.

The compounds which are particularly useful for raising antibodies, whether alone or bound to a suitable carrier are those represented by formula (I)

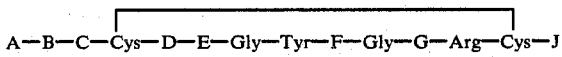 (III)

wherein
A is hydrogen;
B is bond;
C is $(Gly)_x$ or $(Ala)_x$ where x is 0, 1 or 2;
E is Ser;
F is Val;
G is Val or Ala; and
J is $NH_2$.

Either monoclonal or polyclonal antibodies may be used in the diagnostic practice of this invention. There are numerous means known in the art for producing polyclonal antibodies to an antigen or hapten, all of which may be used in this invention.

Monoclonal antibodies useful in the method of the invention may be produced according to the standard techniques of Köhler and Milstein, *Nature,* 265:495–497, 1975 or any of the improved methodologies developed based on that art. For example the peptides coupled to a suitable carrier protein are used as immunogen and administered to a mouse. After a sufficient time, the mouse is sacrificed and spleen cells obtained. The spleen cell chromosomes encoding the base sequences for the desired immunoglobulins are immortalized by fusing the spleen cells with myeloma cells or with lymphoma cells, generally in the presence of a non-ionic detergent, for example polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., a microtiter well, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies, so as to free the monoclonal antibodies from other proteins and other contaminants (see Köhler and Milstein, supra).

Those antibodies having functional equivalency with the antibodies obtained by the above description, whether from a murine source, mammalian source including human, or other sources, or combinations thereof are included within the scope of this invention, and include all classes such as IgG, IgA, IgD, IgE, and IgM, or the like, including isotypes within such classes. By the term "functional equivalency" is meant that the antibody is capable of binding to the compound of this invention and block the binding of another antibody of this invention.

Immunoglobulins specific for the antibody employed may be raised according to standard techniques by injecting a suitable host with the monoclonal antibody, waiting for an appropriate time, and harvesting the anti-mouse immunoglobulins from the blood of the injected host.

Once the antibodies of this invention are obtained, one determines the presence of human TFGα in a specimen by contacting the specimen with the antibody under conditions for binding the antibody to TGFα in the specimen, then observing the degree of binding of the antibody to TGFα.

To observe the presence of binding between the antibody and TGFα in the specimen where a fluorophore is used, one may examine the slide for fluorescence, usually employing a fluorescence microscope. Where a label other than a fluorophore is employed, one may examine the slide or the specimen for the formation of a precipitate, a color, radioactivity or the like.

The antibodies of the invention may be used in all assays involving antigen-antibody reactions. The contact in the method of this invention may be in a homogeneous or heterogeneous system. In a homogeneous assay approach, the specimen is clarified to remove debris, if necessary. The immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and the like.

In a heterogeneous assay approach, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal includes the use of radioactive labels, fluorophore, enzymes, and so forth. Exemplary of heterogeneous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

ELISA refers to an enzyme-linked-immunoabsorbent assay which employs an antibody or antigen bound to a solid phase and an enzyme-antigen or enzyme-antibody conjugate to detect and quantify the amount of antigen or antibody present in a sample. A description of the ELISA technique is found in Chapter 22 of the Fourth Edition of *Basic and Clinical Immunology*, by D. P. Sites, et al., published by Lang Medical Publications of Los Altos, Calif. in 1982, and U.S. Pat. Nos. 3,654,090; 3,850,752; and 4,016,043, all of which are incorporated herein by reference. The EMIT technique refers to an enzyme-multiplied immunoassay technique which uses (1) an enzyme-labeled hapten, (2) specific antibody to the hapten, (3) pretreatment reagent, (4) buffered—enzyme substrate and (5) standards to detect the amount of an unknown in a sample. A description of the EMIT technique is found in *Enzyme Immunoassay*, edited by E. T. Maggio, published in 1980 by C.R.C. Press, Inc., Boca Raton, Fla., particularly on pages 141–150, 234–5 and 242–3.

Radioimmunoassay or RIA refers to an antibody-based assay in which the ligand to be measured displaces or competes for binding with a radio-labeled ligand in an antibody-ligand complex. The complex is separated and the percentage of bound radio-ligand gives a measure of the amount of non-radioactive ligand.

An additional aspect of the present invention relates to the property of certain novel compounds of this invention, i.e., they bind to EGF receptors but have none of the cell proliferation effects of TGF α and EGF. Without mitogenic activity, such compounds are antagonists of the mitogenic effect of TGF α and EGF and are therefore useful therapeutic agents.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use by vaginal or rectal administration particularly in semi-solid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in *Remington's Pharmaceutical Sciences*, Mack Publishing Company, Easton, PA., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinized starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, aliginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix pellets, particularly for use in animals. Additional slow release, depot or implant formulations, e.g. liposomes, are well known in the literature. See, for example, *Sustained and Controlled Release Drug Delivery Systems*, J. R. Robinson ed., Marcel Dekker, Inc., New York, 1978.

SYNTHESIS OF THE PEPTIDES

The polypeptides of the present invention are synthesized by any techniques that are known to those skilled in the peptide art. An excellent summary of the many techniques so available may be found in J. M. Stewart and J. D. Young, *Solid Phase Peptide Synthesis*, W. H. Freeman Co., San Francisco, 1969, and J. Meienhofer, *Hormonal Proteins and Peptides*, Vol. 2, p. 46., Academic Press (New York), 1973 for solid phase peptide synthesis and E. Schroder and K. Lubke, *The Peptides*, Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected (also referred to s "derivatized") amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

PREFERRED EMBODIMENTS OF SYNTHESIS

A particularly preferred method of preparing compounds of the present invention involves solid phase peptide synthesis.

In this particularly preferred method the $\alpha$-amino function of the amino acids is protected by an acid or base-sensitive group. Such protecting groups should have the properties of being stable to the conditions of peptide linkage formation, while being readily removable without destruction of the growing peptide chain or racemization of any of the chiral centers contained therein. Suitable protecting groups are t-butoxycarbonyl (Boc), benzyloxycarbonyl (Cbz), biphenylisopropyloxycarbonyl, t-amyloxycarbonyl, isopropyloxycarbonyl, 1,1-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butoxycarbonyl (Boc).

Particularly preferred side chain protecting groups are, for arginine: nitro, p-toluenesulfonyl, 4-methoxybenzenesulfonyl, Cbz, Boc and adamantyloxycarbonyl; for tyrosine:benzyl, o-bromobenzyloxycarbonyl, 2,6-dichlorobenzyl, isopropyl, cyclohexyl, cyclopentyl and acetyl; for serine:benzyl and tetrahydropyranyl; for histidine:benzyl, p-toluenesulfonyl and 2,4-dinitrophenyl; for cysteine: Bzl, p-MeO-Bzl, ethylcarbamoyl, or acetamidomethyl(Acm).

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be an amide, a particularly useful support is the benzhydrylamino-polystyrene-divinylbenzene polymer described by P. Rivaille, et al, *Helv. Chim. Acta.*, 54, 2772 (1971). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichloromethane. The coupling of successive protected amino acids can be carried out in an automatic polypeptide synthesizer as is well known in the art. The removal of the N$^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide (DIC) or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide may be removed from the resin. When the linkage to the resin support is of the benzyl ester type, cleavage is by means of aminolysis with an alkylamine or fluoroalkylamine for peptides with an alkylamide C-terminus, or by ammonlysis with, for example, ammonia/methanol or ammonia/ethanol for peptides with an amide-blocked C-terminus at a temperature between about 10° and 50° C., preferably about 25° C., for between about 12 and 24 hours, preferably about 18 hours. Alternatively, the peptide may be removed from the resin by trans-esterification, e.g., with methanol, followed by aminolysis. The protected peptide may be purified at this point by silica gel chromatography. The removal of the side chain protecting groups for the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride and anisole at a temperature between about −10° and +10° C., preferably about 0° C., for between about 15 minutes and 1 hour, preferably about 30 minutes. Alternatively, the peptide may be obtained with a free carboxylic acid C-terminus by concommitant cleavage from the benzylester type resin and deprotection with liquid HF. The fully deprotected polypeptide is then purified by sequence of chromatographic steps employing any or all of the following types: ion exchange on a weakly basic resin in the acetate form; hydrophobic absorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecyl-silyl-silica bonded phase column packing. Similarly, deprotection and cleavage of the peptide from the benzhydrylamino resin with liquid HF and purification as described above yields the corresponding peptide amide.

PREPARATION 1

This preparation describes a method for preparing esters of N$^\alpha$-benzyloxycarbony-N,N'-guanidino-diaklyl-homoarginates and the corresponding N,N'-guanidino-dialkyl-homoarginates which are used to prepare compounds of formula (I) in which B and I may be represented by the radical of formula (II) wherein R$_2$ is hydrogen, alkyl, lower fluoroalkyl, cycloalkyl or phenyl and R$_1$ is —NRR$_3$ where R is hydrogen and R$_3$ is alkyl, lower fluoroalkyl, cycloalkyl or phenyl.

A. A mixture of 5.24 g of benzyl N$^\alpha$-benzyloxycarbonyl-D-lysinate toluenesulfonate (B. Bezus and L. Zervas, J. Am. Chem. Soc., 83, 719 (1961)) and 1.72 ml of diisopropylethylamine in 60 ml of dioxane is treated with 1.89 g of N,N'-diisopropylcarbodiimide. The reaction mixture is stirred at 100° C. for 6 hours, cooled to room temperature and concentrated to a solid. The solid is suspended in 20 ml of warm dimethylformamide (DMF), filtered to remove N,N'-diisopropylurea and the filtrate concentrated to a solid. Benzyl N$^\alpha$-benzyloxycarbonyl-N,N'-guanidino-diisopropyl-D-homoarginate toluenesulfonate is obtained as a white solid by crystallization from methanol/ethyl acetate $[\alpha]_D^{25} -7.26°$ (C 0.3, MeOH).

B. Similarly, by using the above procedure, but substituting:
N,N'-dimethylcarbodiimide;
N,N'-diethylcarbodiimide;
N,N'-di-n-propylcarbodiimide;
N,N'-di-i-propylcarbodiimide;
N,N'-di-n-butylcarbodiimide;
N,N'-di-i-buylcarbodiimide;
N,N'-di-n-pentylcarbodiimide;
N,N'-di-i-pentylcarbodiimide;
N,N'-di-n-hexylcarbodiimide;
N,N'-dicyclohexylcarbodiimide;
N,N'-diphenylcarbodiimide;
N,N'-ditolylcarbodiimide;
N-ethylcarbodiimide;
N-propylcarbodiimide;
1-(3-dimethylaminopropyl)-3-ethylcarbodiimide-HCl;
or
N,N'-bis(2,2,2-trifluorodiethyl)carbodiimide;
and the like for N,N'-diisopropyl carbodiimide, the following compounds are obtained:
benzyl N$^\alpha$-benzyloxycarbonyl-N,N'-guanidino-dimethyl-D-homoargininate, $[\alpha]_D^{25}$ 8.07° (C 0.9 MeOH);
benzyl N$^\alpha$-benzyloxycarbonyl-N,N'-guanidino-diethyl-D-homoargininate;
benzyl N$^\alpha$-benzyloxycarbonyl-N,N'-guanidino-di-n-propyl-D-homoarginate;
benzyl N$^\alpha$-benzyloxycarbonyl-N,N'-guanidino-diisopropyl-D-homoargininate;
benzyl N$^\alpha$-benzyloxycarbonyl-N,N'-guanidino-di-n-butyl-D-homoargininate;
benzyl N$^\alpha$-benzyloxycarbonyl-N,N'-guanidino-di-i-butyl-D-homoarginate;
benzyl N$^\alpha$-benzyloxycarbonyl-N,N'-guanidino-di-n-pentyl-D-homoargininate;
benzyl N$^\alpha$-benzyloxycarbonyl-N,N'-guanidino-di-i-pentyl-D-homoargininate;
benzyl N$^\alpha$-benzyloxycarbonyl-N,N'-guanidino-di-n-hexyl-D-homoargininate;
benzyl N$^\alpha$-benzyloxycarbonyl-N,N'-guanidino-dicyclohexyl-D-homoargininate, $[\alpha]_D^{25}$ 8.07° (C0.9, MeOH);
benzyl N$^\alpha$-benzyloxycarbonyl-N,N'-guanidino-diphenyl-D-homoargininate;
benzyl N$^\alpha$-benzyloxycarbonyl-N-N'-guanidino-ditolyl-D-homoargininate;

benzyl N$^\alpha$-benzyloxycarbonyl-N-guanidino-ethyl-D-homoarginate;

benzyl N$^\alpha$-benzyloxycarbonyl-N-guanidino-N'-propyl-D-homargininate;

benzyl N$^\alpha$-benzyloxycarbonyl, N-guanidino-(3-dimethylaminopropyl)-N'-guanidino-ethyl-D-homarginate;

benzyl N$^\alpha$-benzylcarbonyl-N,N'-guanidino-di(2,2,2-trifluoroethyl)-D-homargininate; and the like as their benzenesulfonate salts.

C. Similarly, by substituting benzyl N$^\alpha$-benzyloxycarbonyl-D-ornithinate toluenesulfonate for the D-lysinate in parts A and B there are obtained the corresponding D-arginine analogs as their toluenesulfonate salts.

D. Similarly by following the procedure of Parts A, B and C, but substituting benzyl N$^\alpha$-benzyloxycarbonyl-L-lysinate toluenesulfonate and benzyl N$^\alpha$-benzyloxycarbonyl-L-ornithinate toluenesulfonate for the corresponding D-isomers, the L-isomers which correspond to the D-isomers of Part A, B and C are prepared, for example:

benzyl N$^\alpha$benzyloxycarbonyl-N,N'-guanidino-diethyl-L-homarginiate toluensulfonate benzyl N$^\alpha$-benzyloxycarbonyl-N-N'-guanidino-diethyl-L-argininate toluenesulfonate, and the like.

PREPARATION 2

A. Benzyl N$^\alpha$-benzyloxycarbonyl-N$^G$,N$^{G'}$-ethylene-D-homargininate

To a mixture of 15 ml of toluene and 15 ml of t-BuOH was added 2.71 g of benzyl N$^\alpha$-benzyloxycarbonyl-D-lysinate and 1.46 g of 2-methylthioimidazoline.HI (available from Aldrich). The pH of the mixture was brought to ~8 by the addition of diisopropylethylamine and the solution heated under reflux for 24 hours.

The solution was concentrated in vacuo and the residue was loaded on a silica gel column (250 g). The column was eluted with a gradient from CH$_2$Cl$_2$/MeOH (19:1) to CH$_2$Cl$_2$/MeOH (7:3). The fractions containing product were detected by TLC, pooled, and concentrated to dryness, to yield 2.9 g of benzyl N$^\alpha$-benzyloxycarbonyl-N$^G$,N$^{G'}$-ethylene-D-homargininate as a white foam.

A 2 g portion of the above-named product was dissolved in 50 ml of ethanol containing 0.8 g of 10% Pd/C. The solution was stirred under H$_2$ for 8 hours. The mixture was filtered on celite and the filtrate was concentrated to dryness to give N$^G$,N$^{G'}$-etheno-D-homoarginine as a white foam, 1.2 g.

B. N$^\alpha$-Boc$^G$-N$^{G'}$,N-ethylene-D-homoarginine

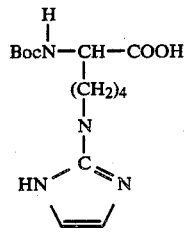

A solution of 2.74 g of D-lysine dihydrochloride and 4.03 g of 2-methylthio-2-imidazoline.hydroiodide in 16.5 ml of 2N NaOH was stirred at room temperature for 6 days. Analysis of the reaction mixture on an amino acid analyzer showed that ~70% of the desired ε-dialkylguanidino compound had been formed. A further 0.25 g of the 2-methylthio-2-imidazoline.hydroiodide and 1 ml of 2N NaOH were added and the reaction was continued at room temperature for 3 more days.

The reaction mixture was treated with 0.8 g MgO and 4.36 g of di-tert-butyldicarbonate in 20 ml of dioxane. The pH was adjusted to 9.5 with 1N NaOH. After overnight reaction some starting material was present, so 1 g of di-tert-butyldicarbonate was added.

The mixture was filtered and the filtrate was concentrated to dryness. The residue was dissolved in H$_2$O and washed with diethyl ether and the aqueous layer was adjusted to pH 4 with acetic acid. The acidic solution was washed with ethyl acetate. The aqueous layer containing the product was treated with anion exchange resin (AG-3 acetate, BioRad) and concentrated to dryness.

The crude product was passed through a hydrophobic chromatography column (Amberlite XAD-2, Rohm & Haas) by elution with a gradient from H$_2$O to 25% ethanol. The fractions containing product were pooled to yield 2.7 g of N$^\alpha$-Boc-N$^G$,N$^{G'}$-ethylene-D-homoarginine, $[\alpha]_D^{25} -19.7°$ (c 0.1, MeOH).

C. In a fashion similar to Part B, by substituting:
S-methyl-diethyl-iso-thiourea-HI,
S-methyl-dipropyl-iso-thiourea-HI,
S-methyl-dibutyl-iso-thiourea-HI,
S-methyl-dipentyl-iso-thiourea-HI,
S-methyl-dihexyl-iso-thiourea-HI,
S-methyl-diheptyl-iso-thiourea-HI,
S-methyl-dinonyl-iso-thiourea-HI,
S-methyl-diphenyl-iso-thioura-HI,
S-methyl-N-methyl-N'-propyl-iso-thiourea-HI,
S-methyl-N-methyl-N'-butyl-iso-thiourea-HI, and
S-methyl-N-methyl-N'-hexyl-iso-thiourea-HI,
S-methyl-N-ethyl-iso-thiourea-HI
for 2-methylthio-2-imidazoline-HI, there are obtained:
N$^\alpha$-Boc-N,N'-guanidino-diethyl-D-homoarginine, $[\alpha]_D^{25} -19.7°$ (C 0.1, MeOH);
N$^\alpha$-Boc-N,N'-guanidino-dipropyl-D-homoarginine, $[\alpha]_D^{25} -11.3°$ (C 0.5, MeOH);
N$^\alpha$-Boc-N,N'-guanidino-dibutyl-D-homoarginine, $[\alpha]_D^{25} -6.3°$ (C 0.5, MeOH)
N$^\alpha$-Boc-N,N'-guanidino-dipentyl-D-homoarginine,
N$^\alpha$-Boc-N,N'-guanidino-dihexyl-D-homoarginine, $[\alpha]_D^{25}$,
N$^\alpha$-Boc-N,N'-guanidino-diheptyl-D-homoarginine,
N$^\alpha$-Boc-N,N'-guanidino-dinonyl-D-homoarginine,
N$^\alpha$-Boc-N,N'-guanidino-diphenyl-D-homoarginine, $[\alpha]_D^{25} -9.2°$ (C 0.8, MeOH);
N$^\alpha$-Boc-N,N'-guanidino-methyl,ethyl-D-homoarginine,
N$^\alpha$-Boc-N,N'-guanidino-methyl,propyl-D-homoarginine,
N$^\alpha$-Boc-N,N'-guanidino-methyl,butyl-D-homoarginine,
N$^\alpha$-Boc-N,N'-guanidino-methyl,hexyl-D-homoarginine, and $[\alpha]_D^{25} -2.2$ (C 0.4, EtOH), and
N$^\alpha$-Boc-N-guanidino-ethyl-D-homoarginine, respectively D. By following the procedures set forth in Parts A, B and C but substituting benzyl N$^\alpha$-benzoyloxycarbonyl-D-ornithininate for benzyl N$^\alpha$-benzyloxycarbonyl-D-lysinate and D-ornithine dihydrochloride for D-lysine dihydrochloride, compounds are prepared in the D-arginine series such as
N$^G$N$^{G'}$-etheno-D-arginine,
N$^\alpha$-Boc-N$^G$,N$^{G'}$-ethylene-D-arginine, N$^\alpha$-Boc-N,N'-guanidino-diethyl-D-arginine, and the like.

E. By following the procedures set forth in Parts A, B, C and D but substituting benzyl N$^\alpha$-benzyloxycarbonyl-L-lysinate or benzyl N$^\alpha$-benzyloxycarbonyl-L-ornithinate for benzyl N$^\alpha$-benzyloxycarbonyl-D-lysinate; and L-lysine dihydrochloride or L-ornithine dihydrochloride for D-lysine dihydrochloride, compounds are prepared in the L-homoarginine or L-arginine series such as N$^G$,N$^{G'}$-etheno-L-homoarginine,
N$^G$,N$^{G'}$-etheno-L-arginine,
N$^\alpha$-Boc-N$^G$,N$^{G'}$-ethylene-L-homoarginine,
N$^\alpha$-Boc-N$^G$,N$^{G'}$-ethylene-L-arginine,
N$^\alpha$-Boc-N,N'-guanidino-diethyl-L-homarginine,
N$^\alpha$-Boc-N,N'-guanidino-diethyl-L-arginine, and the like.

PREPARATION 3

A. This preparation illustrates the preparation of N,N'-guanidino-disubstituted-D-homoarginines as their toluenesulfonate salts.

A mixture of benzyl N$^\alpha$-benzyoxycarbonyl-N,N'-guanidino-diisopropyl-D-homoargininate toluenesulfonate (3.25 g) and 100 mg of 10% Pd/C in 50 ml of glacial acetic acid is treated with hydrogen gas at atmospheric pressure for 4 hours. The catalyst is filtered on celite and the filtrate is concentrated to a solid, N,N'-guanidino-diisopropyl-D-homoarginine toluenesulfonate, $[\alpha]_D^{25} -3.5°$ (C 0.5, MeOH).

B. Proceeding in a similar manner, but substituting the appropriate toluenesulfonate precursors for benzyl N$^\alpha$-benzyloxycarbonyl-N,N'-guanidino-diisopropyl-D-homoarginate, other N,N'-guanidino-disubstituted-D-homoarginines, -D-arginines and their L-analogs, or similar analog, there may be prepared, for example, the following compounds:

N,N'-guanidino-diisopropyl-D-homoarginine,
  $[\alpha]_D^{25} -10.5°$ (C 0.4, MeOH);
N,N'-guanidino-di(cyclohexyl)-D-homoarginine,
  $[\alpha]_D^{25} -7.6°$ (C 0.1, MeOH);
N,N'-guanidino-diphenyl-D-homoarginine,
  $[\alpha]_D^{25} -11.7°$ (C 0.5, MeOH)
N,N'-guanidino-di(n-propyl)-D-homoarginine,
  $[\alpha]_D^{25} -7.1°$ (C 0.4, MeOH)
N,N'-guanidino-diethyl-D-homoarginine, $[\alpha]_D^{25}, -6.0°$
  (C 0.1, MeOH)
N,N'-guanidino-di(n-hexyl)-D-homoarginine,
  $[\alpha]_D^{25} -8.3°$ (C 0.3, MeOH)
N,N'-guanidino-di(n-butyl)-D-homoarginine,
  $[\alpha]_D^{25} -6.3°$ (C 0.5, MeOH);

PREPARATION 4

N$^\alpha$-Boc-3-(4'-(1'-propylpiperidyl))-D-alanine

A 4.6 g portion of sodium metal was added to 400 ml of absolute ethanol and heated. To the resultant solution of sodium ethoxide was added 21.7 g of diethyl acetamidomalonate and 16.4 g of 4-picolyl chloride hydrochloride (Aldrich Chem. Co.). The reaction mixture was heated to 100° C. for 4 hours, cooled filtered and concentrated in vacuo. The mixture was loaded on a silica gel column in methylene chloride/methanol (19:1) and eluted with the same mixture. The product was located as a fast-running UV positive spot by TLC on silica gel in methylene chloride/methanol (19:1). Combined fractions were concentrated to provide the product.

The product from the foregoing paragraph was dissolved in 200 ml of ethanol and treated with a solution of 2.72 g of sodium hydroxide in 40 ml of water at 50° C. for 6 hours. The solution was acidified with 12 ml of 6N HCl, concentrated to dryness and taken up in 200 ml of dioxane. The suspension was filtered and the filtrate heated at reflux for 2 hours. The solution was cooled and concentrated to dryness to yield ethyl N$^\alpha$-acetyl-3-(4-pyridyl)-D,L-alanine as a white solid.

A portion of this N-acetyl ester was resolved by treatment with 200 ml of the enzyme subtilisin Carlsberg (Sigma Chem. Co., protease VIII) in a mixture of 300 ml of dimethyl sulfoxide and 400 ml of 0.01M KCl (pH 7.2). The pH was maintained by addition of 1N NaOH on a pH stat. After a 6 hour period, the resolution was complete. The solution was diluted with 400 ml of water and extracted with 4×750 ml of ethyl acetate. The organic layers were combined and dried over magnesium sulfate and concentrated to yield ethyl N$^\alpha$-acetyl-3-(4-pyridyl)-D-alaninate as an oil.

The oil was reacted with 1.22 g of n-propyl bromide in 50 ml of ethanol after which the solution was concentrated to dryness to yield ethyl N$^\alpha$-acetyl-3-(1-propyl-pyridinium-4-yl)-D-alininate bromide as a white hygroscopic solid.

This white solid was dissolved in 200 ml of ethanol and was reduced under an atmosphere of hydrogen gas using 100 mg of 10% Pd/C as a catalyst. After an 18 hour reduction period, the catalyst was filtered out and the solutin concentrated to yield ethyl N$^\alpha$-acetyl-3-(4'-(1'-propylpipeidyl)-D-alininate as a tan solid.

The free acid was prepared by refluxing the ethyl ester in 100 ml of 6N HCl for 4 hours to yield 3-(4'-(1'-propyl-piperidyl))-D-alanine as a white solid.

The free acid was dissolved in 100 ml of dioxane/water (1:1) and treated with 2 g of di-t-butyldicarbonate. The pH was maintained at 9 by addition of 1N NaOH on a pH stat. After 2 hours the reaction muxture was concentrated in vacuo, washed with 100 ml of ethyl ether and the aqueous laye was loaded on an Amberlite XAD-2 hydrophobic resin. The column was eluted with 250 ml of water followed by 250 ml of 50% ethanol/water. The ethanol eluate was pooled and concentrated to dryness to yield N$^\alpha$-t-butyloxycarbonyl-3-(4'-(1'-propylpiperidyl))-D-alanine as a white solid.

Proceeding in similar manner, but substituting 3-picolyl chloride hydrochloride for 4-picolyl chloride hydrochloride, there is prepared N$^\alpha$-t-butyloxycarbonyl-3-(3'-(1'-propylpiperidyl))-D-alanine.

EXAMPLE 1

This example describes a method for preparing compounds of formula I where A is hydrogen, B is a bond, C is a bond (i.e. x is 0); D is Val or His; E is Ile, Val or Ser; F is Val, Ser or Ile; G is Val, Ala, Asp or Glu; H is a bond (i.e. x is 0); I is a bond; and J is OH.

A. Boc-Cys-(BzlOMe)-O-Resin, 2.254 g, containing 2 mmol of cystine was placed in the reaction vessel of a Beckman 990 Peptide Synthesizer. Using the standard coupling program for the 990 synthesizer, the following amounts of amino acids were incorporated sequentially:
2.14 g Boc-Arg(Tos)-OH;
1.086 g Boc-Val-OH;
0.88 g Boc-Gly-OH;
1.086 g Boc-Val-OH;
1.75 g Boc-Tyr(2,6-Cl$_2$-Bzl)-OH;
0.88 g Boc-Gly-OH;

1.48 g Boc-Ser(Bzl)-OH;
2.05 g Boc-His(Tos)-OH; and
1.72 g Boc-Cys(BzlOMe)-OH;

The protected polypeptide resin was dried in vacuo and deprotected by treatment with anhydrous liquid HF in the presence of 10% anisole at 0° C. for 1 hour. The HF was removed in vacuo and the residue was washed with 3×30 ml diethyl ether. The deprotected polypeptide was extracted from the residue with 3×40 ml of glacial acetic acid and the extract was filtered to remove the resin. The acetic acid was removed in vacuo on a rotary evaporator and the residue dissolved in water and passed through a weakly basic ion exchange resin (BioRad-Ag3: acetate form) to change the counter-ion from the fluoride ion to acetate ion. The solution was lyophilyzed to yield 800 mg of a white fluffy powder.

This crude product was cyclized to the monomeric disulfide form by oxidation using $ICH_2CH_2I$ (other oxidants such as atmospheric oxygen, $I_2$, Fe(III) and the like may similarly be used). Thus, a 600 mg portion of crude peptide in ~600 ml $H_2O$ (adjusted to pH 8.5 with ammonium hydroxide) was treated with 280 mg of $IC_2CH_2I$ in 3 ml acetone. The reaction mix was allowed to stir overnight at room temperature at which time oxidation was complete. The pH of the solution was adjusted to 4.5 with acetic acid. The solution was concentrated in vacuo on a rotary evaporator and portions of the residue were dissolved in 15% $CH_3CN/85\%$ $H_2O$ (This solvent mixture was 0.03M in ammonium acetate, adjusted to pH 4.5 with acetic acid).

The product was obtained in pure form by preparative high performance liquid chromatography on a 2.5×100 cm column containing 25-40 micron Licroprep ® C-18 (E. Merck) reversed phase packing material using a 15% $CH_3CN$ eluent (0.03M in $NH_4OAc$ pH 4.5) as described above at a flow rate of ~20 ml/min. Purification runs were performed on ~200 mg samples of the crude product. In this manner, ~600 mg of the crude product was processed to yield 120 mg of the pure product having the formula

which decomposed at ~112°; and gave the correct amino acid analysis: Ser, 0.96(1); Gly 2.11(2); Cys, 2.04(2); Val, 1.90(2); Tyr, 0.96(1); His, 1.04(1); Arg, 0.99(1).

B. Following the above procedure but substituting Boc-L-AlaOH, Boc-L-AspOH or Boc-L-GluOH for BOC-L-ValOH in the second coupling there was obtained

(corresponding to residues 34–43 of human TGFα),

and

C. Compounds of formula (I) where D is Val, are prepared by following the procedure of Part A, but substituting Boc-Val-OH for Boc-His(Tos)-OH in the eighth coupling.

D. Compounds of formula (I) where E and F are independently Val, Ile or Ser are prepared by following the procedure of Part A, but substituting Boc-Val-OH or Boc-Ile-OH for Boc-Ser(Bzl)-OH in the seventh coupling (for E) and Boc-Ser(Bzl)-OH or Boc-Ile-OH for Boc-Val-OH in the fifth coupling (for F).

EXAMPLE 2

This example describes a method for preparing compounds of formula (I) wherein A is acyl of one to twelve carbon atoms, benzoyl, 3-(4-hydroxyphenyl)propionyl or 3-(3,5-diiodo-4-hydroxyphenyl)propionyl and J is $NHR_8$ where $R_8$ is hydrogen, lower alkyl or lower fluoroalkyl.

A. Following the procedure of Parts A-D of Example 1 but blocking the N-terminus with acetic anhydride and aminolyzing the peptide from the resin with ethyl amine prior to HF deprotection the following compounds are obtained

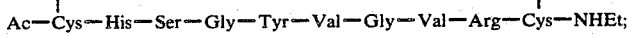

mp. 220°–222° C.

and the like, where Ac is acetyl.

B. By following the procedure of Part A of this Example 2 but substituting other anhydrides such as propionyl anhydride, butyryl anhydride, n-hexanoyl anhydride, benzoic anhydride, Bolton-Hunter reagent or the succinimide ester of 3-(3,5-diiodo-4-hydroxyphenyl)-propionate for acetic anhydride one obtains compounds corresponding to compounds of Part A where Ac is propionyl, butyryl, hexanoyl, benzoyl, 3-(4-hydroxyphenyl)propionyl or 3-(3,5-diiodo-4-hydroxyphenyl)-propionyl, respectively C. By following the procedure of Parts A and B of this Example 2 but replacing ethylamine with methylamine, isopropylamine, t-butylamine, or 2,2,2-trifluoroethylamine the compounds corresponding to Parts A and B are obtained wherein the —NHEt is —NHCH$_3$, —NHCH(CH$_3$)$_2$, —NHC(CH$_3$)$_3$ or —NHCH$_2$CF$_3$.

EXAMPLE 3

This example describes a method for preparing compounds of formula (I) wherein C is (Gly)$_x$ or (Ala)$_x$ wherein x is an integer of 0-5 and H is (Gly)$_y$ or (Ala)$_y$ wherein y is an integer of 0-5.

A. By following the procedure of Example 1, Parts A-D, but in addition reacting the polypeptide formed on the resin with sequential quantities of Boc-Gly-OH or Boc-Ala-OH, one obtains the following representative compounds

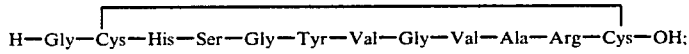
H—Gly—Cys—His—Ser—Gly—Tyr—Val—Gly—Val—Ala—Arg—Cys—OH;

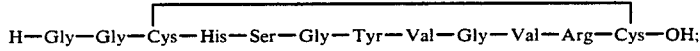
H—Gly—Gly—Cys—His—Ser—Gly—Tyr—Val—Gly—Val—Arg—Cys—OH;

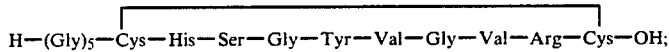
H—(Gly)$_5$—Cys—His—Ser—Gly—Tyr—Val—Gly—Val—Arg—Cys—OH;

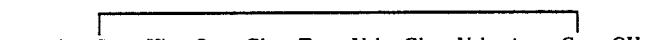
H—Ala—Cys—His—Ser—Gly—Tyr—Val—Gly—Val—Arg—Cys—OH;

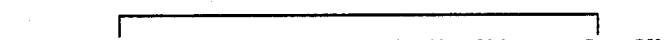
H—(Ala)$_4$—Cys—His—Ser—Gly—Tyr—Val—Gly—Val—Arg—Cys—OH;

B. Following the above procedure of Part A, incorporating two Gly residues and in addition reacting a N$^\alpha$-protected-N,N'-guanidino-substituted-D-homoarginine or D-arginine or the corresponding L-isomers, one obtains other compounds of this invention. For example by using N$^\alpha$-Boc-D-Deh, or N$^\alpha$-Boc-L-Deh, the following compounds are prepared:

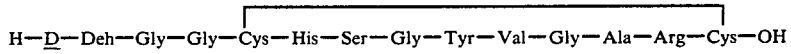
H—D—Deh—Gly—Gly—Cys—His—Ser—Gly—Tyr—Val—Gly—Ala—Arg—Cys—OH of mp 219°–221° C.; [α]$_D^{25}$ −15.8° (CO.3, HOAc), and

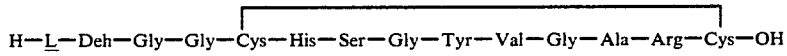
H—L—Deh—Gly—Gly—Cys—His—Ser—Gly—Tyr—Val—Gly—Ala—Arg—Cys—OH of mp 185°–187° C.; [α]$_D^{25}$ −5.7° (CO.3, HOAc).

By following the above procedures of Parts A and B but blocking the N-terminus with an appropriate anhydride such as acetic anhydride and aminolyzing the peptide from the resin with an appropriate amine (e.g., ethylamine) prior to HF deprotection, the following compounds are obtained

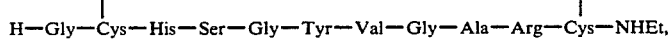
H—Gly—Cys—His—Ser—Gly—Tyr—Val—Gly—Ala—Arg—Cys—NHEt,

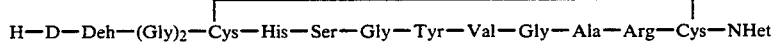
H—D—Deh—(Gly)$_2$—Cys—His—Ser—Gly—Tyr—Val—Gly—Ala—Arg—Cys—NHet and the like.

EXAMPLE 4

This example describes a method for preparing compounds of formula (I) wherein A is acyl of one to twelve carbon atoms and J is NH$_2$.

A. The procedure of Example 1 was followed but 1.52 g of benzhydrylamine resing (1 mmol) for Boc-Cys-(BzlOMe)-o-resin and this resin was sequentially reacted with the following:

0.86 g Boc-Cys(Bzl-OMe)-OH
1.07 g Boc-Arg(Tos)-OH;
0.54 g Boc-Val-OH;
0.44 g Boc-Gly-OH;
0.54 g Boc-Val-OH;
0.88 g Boc-Tyr(2,6-Cl$_2$-Bzl)-OH;
0.44 g Boc-Gly-OH;
0.74 g Boc-Ser(Bzl)-OH;
1.03 g Boc-His(Tos)-OH;
0.86 g Boc-Cys(BzlOMe)-OH; and
0.3 ml Acetic anhydride The protected peptide resin was dried in vacuo and deprotected as described in Example 1. The crude peptide was cyclized by oxidation with ICH$_2$CH$_2$I at pH 9 as described in Example 1. The oxidized product was purified by reversed phase HPLC using a 20% acetonitrile/80% water (0.03M in NH$_4$OAc, pH 4.5) eluent. The pure product

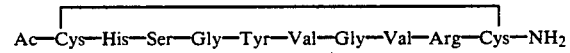
Ac—Cys—His—Ser—Gly—Tyr—Val—Gly—Val—Arg—Cys—NH$_2$ decomposed at ca. 95° C., had an optical rotation of −52.9° (C 1, H₂O) and exhibited the correct amino acid analysis: Ser, 0.97 (1); Gly, 2.07 (2); Cys, 1.87 (2); Val, 1.92 (2); Tyr, 0.96 (1); His, 1.04 (1); Arg, 1.01 (1); and NH₂ 1.36 (1).

Similarly was obtained

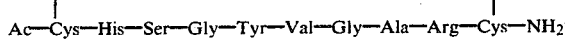

of mp 180°–183° C.; $[\alpha]_D^{25} -27.8°$(C0.4, HOAc).

B. Following the procedure of Part A but first reacting 1.157 g of the benzyldrylamine resin with 0.76 g of Boc-D-DehOH and subsequently adding the sequence of amino acids described above and oxidizing the deprotected peptide there was obtained.

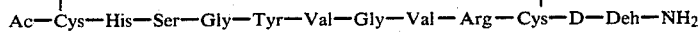

The compound was purified by HPLC as described above using the solvent system 24% CH₃CN/76%H₂O (0.06 m in NH40Ac, pH4.5); Amino acid analysis Ser, 0.92(1); Gly, 1–93(2); Cys, 1.87(2); Val 1.97 (2); Tyr, 1.0(1); His, 1.05(1); NH₃ 1.46(1); Arg 1.05(1); Deh,1.03(1).

EXAMPLE 5

This example describes a method for preparing a compound of formula (I) wherein J is OR₇ wherein R₇ is alkyl of 1 to 12 carbon atoms.

A. The procedure of Example 1, Parts A–D is followed but the N-terminus is blocked with an appropriate anhydride, such as acetic anhydride, as taught in Example 2. In addition, the peptide resin is first treated with a strong base (e.g. triethyl amine) in the presence of an appropriate alcohol of one to twelve carbon atoms (e.g. methanol), the corresponding C-terminus ester is obtained.

Representative compounds include

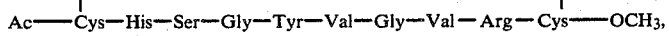

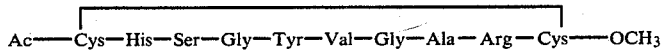

($[\alpha]_D^{25} -19.2°$(C 0.3, HOAc), and other C-terminus alkyl groups including ethyl, proproyl, isopropyl, n-butyl, pentyl, octyl, dodecyl and the like.

EXAMPLE 6

This example describes a method for coupling a compound of formula (I) to a suitable carrier such as keyhole limpet hemocyanin (KLH) or bovine screen albumin (BSA).

A. KLH or BSA from Calbiochem are dissolved in a 100 mM phosphate buffer containing 100 mM NaCl, pH 7.5 and dialyzed against the same buffer. Particulate material is removed by centrifugation.

N-succinimidyl 3-(2-pyriolyldithio)-propionate (SPDP-from Pharmacia) is added to the protein at a 100:1 molar ratio for 30 minutes at room temperature. Excess SPDP is removed by gel filtration on a Sephadex G-25 column equilibrated in a 100 mM sodium acetate buffer, pH 4.5 containing 100 mM NaCl.

Reduction is achieved by addition of 50 mM dithiothreitol for 20 minutes at room temperature under nitrogen bubbling. Proteins are then passed through a Sephadex G25 column equilibrated in 100 mM phosphate buffer, pH 7.5 containing 100 mM NaCl to give the activated carrier.

The product of example 1, Part A

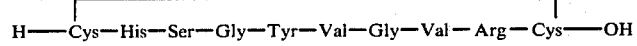

is dissolved in 100 mM phosphte buffer, pH 7.3. Succinimidyl-4-(N-maleimidomethyl)-cyclohexane-1-carboxylate (SMCC-from Pierce Chemical Co.) is dissolved in dimethjylformamide, added to the peptide in a 1:1 molar ratio and incubated on ice for 30 minutes. The resulting mixture is then passed over a Sephadex G-10 column in the phosphate buffer pH 7.3 to give the derivatized peptide.

Activated carrier is combined with derivatized peptide in a 1:100 molar ratio and reacted for 16 hours at 4° C. Carrier-peptide complex is purified on a Sephadex G25 column (modified procedure: King, T. P. and Kochoumian, L. (1979) *J. Immunol. Meth.*, 28, 201). In a representative preparation overall yields are 60% of the carrier-peptide complex with an average of 60 moles peptide/mole KLH and 20 moles peptide/mole BSA.

B. By following the procedure of Part A of this example, but substituting other compounds of formula (I) prepared in accordance with any of the preceding examples, such compounds coupled to suitable carriers are prepared.

EXAMPLE 7

This example describes a method for raising antibodies against a compound of formula (I) which is coupled to a suitable carrier.

Female New Zealand white rabbits are hyperimmunized with the complexes prepared in Part A of Example by injection of 2 mg of the complex at a time per animal.

A solution of the KLH-protein complex (prepared in accordance with Example 6A) and Freund's Complete Adjuvant (1:1) was injected at multiple subcutaneous and intramuscular sites on day 1. Booster injections of the complex and Freund's Incomplete Adjuvant (1:1) were made on days 15, 30, 45 and 60.

Animals were bled by ear vein puncture on day 30 after day 0 and every two weeks thereafter.

IgG fractions from sera were prepared by ion exchange chromatography on DEAE cellulose using the technique of A. B. Schreiber and J. Haismovich Methods in Enzymology, Vol. 93, pp. 147–155 (1983).

EXAMPLE 8

A. Rabbit IgG antibodies to the compound

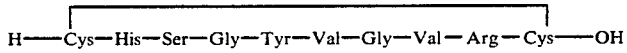
H—Cys—His—Ser—Gly—Tyr—Val—Gly—Val—Arg—Cys—OH (anti-TGF α-KLH), as prepared in accordance with Example 7, were iodinated by the chloramine-T method. To 1 mg anti-TGF α-KLH antibody in 0.2M phosphate buffer (pH 7.6) was added 20 μl of a 2 mg/ml solution of chloramine-T and 1mCiNa$^{125}$I for 3 minutes at room temperature. 1 mg KI was added and excess free iodine removed by chromatography on a Sephadex G-50 column. The specific activity of the antibodies varied between 200,000 and 400,000 counts per minute (cpm)/μg protein. Flexible polyvinylchloride plates were coated with a 1 mg/ml solution of BSA-peptide complex (prepared in accordance with Example 6A) in phosphate buffered saline (PBS) for 16 hours at 4° C. Plates were countered with a solution containing BSA and 1% Bovine gamma globulin.

100,000 Cpm of iodinated rabbit anti-TGF α-KLHIgG were incubated at 37° C. for 2 hours with increasing concentrations of either native h-TGF αor EGF. These solutions were then added to the coated wells for an additional 2 hours at 37° C. After several washes with PBS containing 0.1% BSA, individual wells were cut apart and counted in a gamma counter. The results are given in Table I.

TABLE

| Assay Results | | |
| --- | --- | --- |
| Inhibitor | | cpm |
|  |  | 8400 ± 600 |
| TGFα | 1 ng/ml | 8600 ± 800 |
|  | 10 ng/ml | 7600 ± 400 |
|  | 100 ng/ml | 5100 ± 700 |
|  | 1000 ng/ml | 3800 ± 400 |
| EGF | 10 ng/ml | 8800 ± 400 |
|  | 100 ng/ml | 8200 ± 500 |
|  | 1000 ng/ml | 7600 ± 800 |
|  | 10,000 ng/ml | 7800 ± 600 |
| control (no antigen) |  | 800 ± 100 |

EXAMPLE 9

Competitive Antagonism of Binding by TGFα-Fragments

Murine lung endothelial cells identified as LE II were grown to confluence in 24 well cluster dishes in Dulbecco's minimal essential medium (DMEM) containing 10% fetal calf serum. Cells were washed twice with DMEM containing 1% bovine serum albumin and buffered at pH 7.4 with 50 mM Hepes buffer (DMEM-BSA). Cells were incubated at 4° C. for one hour with increasing concentrations of $^{125}$I-EGF in the absence or presence of 20 μg/ml of each of the following peptides

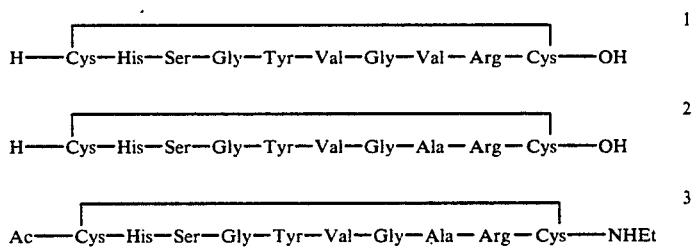

in a final volume of 250 μl DMEM-BSA. At the end of the incubation period, cells were washed three times with DMEM-BSA, lysed in 0.1N sodium hydroxide and cell-associated radioactivity was determined in a gamma counter.

Scatchard plots calculated from these data show an extrapolated saturation binding of 0.51±0.03 nM $^{125}$I-EGF in the absence of

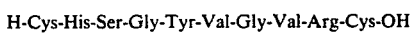
H-Cys-His-Ser-Gly-Tyr-Val-Gly-Val-Arg-Cys-OH and 0.5±0.02 nM $^{125}$I-EGF in the presence of

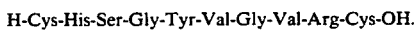
H-Cys-His-Ser-Gly-Tyr-Val-Gly-Val-Arg-Cys-OH.

The apparent association constant for EGF drops from $4 \times 10^{10}$ M$^{-1}$ to $1.5 \times 10^{10}$M$^{-1}$ in the presence of compounds 1 and 2, and to $3 \times 10^8$M$^{-1}$ in the presence of compound 3. The lower the apparent association constant, the more effective is the compound in competitively binding with EGF.

EXAMPLE 10

Inhibition of EGF- and TGFα-Induced Cell Proliferation by compounds of formula (I)

This assay was set up and carried out as follows for both EGF and TGFα inhibition studies. LE II cells were grown to confluence in 48 well cluster dishes and starved for two days in DMEM containing 0.5% fetal calf serum. Ten ng/ml of either EGF or TGFα was added to the cells in the absence or presence of increasing concentrations of the following compounds:

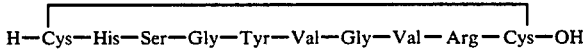
H—Cys—His—Ser—Gly—Tyr—Val—Gly—Val—Arg—Cys—OH

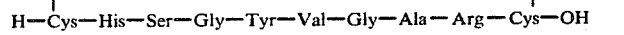

2

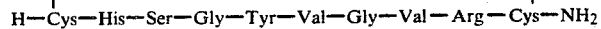

3

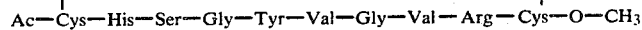

4

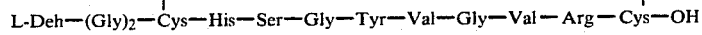

5

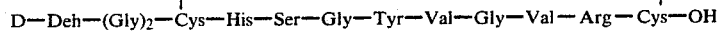

6

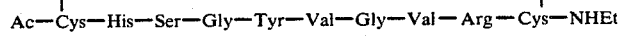

7 for 18 hours at 37° C. prior to a 4 hour pulse with 0.5 μCi [³H]-methylthymidine and determination of trichloroacetic acid-precipitable radioactivity.

The percent enhancement of thymidine incorporation was used as the measure of cell proliferation. The lower the percentage of thymidine incorporation, the lower the rate of cell proliferation. Inhibition of EGF-induced cell proliferation by the foregoing compounds is reflected in Table II. Table III gives the inhibition of TGFα-induced cell proliferation.

TABLE II
Inhibition of Cell Proliferation Induced by $2 \times 10^{-9}$ M EGF

| Peptide | Concentration (M) | % Enhancement of thymidine incorporation* | |
|---|---|---|---|
| (Control) | $10^-$ | 380 ± 20 | 100 |
| 1 | $10^{-7}$ | 3% ± 20 | 103 |
|  | $10^{-6}$ | 360 ± 20 | 95 |
|  | $10^{-5}$ | 265 ± 15 | 70 |
| 2 | $10^{-7}$ | 380 ± 20 | 100 |
|  | $10^{-6}$ | 370 ± 15 | 97 |
|  | $10^{-5}$ | 245 ± 25 | 64 |
| 3 | $10^{-7}$ | 320 ± 30 | 84 |
|  | $10^{-6}$ | 210 ± 20 | 55 |
|  | $10^{-5}$ | 110 ± 20 | 29 |
| 4 | $10^{-7}$ | 220 ± 40 | 58 |
|  | $10^{-6}$ | 110 ± 20 | 29 |
|  | $10^{-5}$ | 40 ± 10 | 11 |
| 5 | $10^{-7}$ | 190 ± 20 | 50 |
|  | $10^{-6}$ | 100 ± 20 | 26 |
|  | $10^{-5}$ | 70 ± 10 | 18 |
| 6 | $10^{-7}$ | 205 ± 15 | 54 |
|  | $10^{-6}$ | 90 ± 15 | 24 |
|  | $10^{-5}$ | 60 ± 10 | 16 |
| 7 | $10^{-7}$ | 240 ± 20 | 63 |
|  | $10^{-6}$ | 110 ± 25 | 29 |
|  | $10^{-5}$ | 80 ± 20 | 21 |

*Calculated as the ratio of TGF α fragment/EGF counts per minute.

TABLE III
Inhibition of Cell Proliferation Induced by $2 \times 10^{-9}$ M TGFα

| Peptide | Concentration (M) | % of thymidine incorporation | |
|---|---|---|---|
| Control | 0 | 420 ± 30 | 100 |
| 1 | $10^{-7}$ | 400 ± 20 | 95 |
|  | $10^{-6}$ | 400 ± 20 | 95 |
|  | $10^{-5}$ | 330 ± 20 | 79 |
| 6 | $10^{-7}$ | 240 ± 30 | 57 |
|  | $10^{-6}$ | 180 ± 20 | 43 |
|  | $10^{-5}$ | 105 ± 15 | 25 |

What is claimed is:
1. A compound represented by the formula

$$A—B—C— \quad (I)$$

—Cys—D—E—Gly—Tyr—F—Gly—G—Arg—Cys—

—H—I—J, the reduced form of said compound or a pharmaceutically acceptable salt of said compound, wherein A is hydrogen, acyl of one to twelve carbon atoms, benzoyl, 3-(4-hydroxyphenyl)propionyl, or 3-(3,5-diiodo-4-hydroxyphenyl)propionyl;

B is a bond or a radical of the formula $$\begin{array}{c} -HN-CH-CO- \\ | \\ (CH_2)_n \\ | \\ NH \\ | \\ R_1-C=NR_2; \end{array} \quad (II)$$

C is $(Gly)_x$ or $(Ala)_x$;
D is Val or His;
E is Ser, Ile or Val;
F is val, Ser or Ile;
G is Val, Ala, Asp or Glu;
H is $(Gly)_y$ or $(Ala)_y$;
I is a bond or a radical represented by formula (II), but independent thereof; and
J is $OR_7$ or $NHR_8$,
wherein for B, C, H, I and J
n is an integer of two to five; each of x and y is independently an integer of zero to five;
$R_1$ is alkyl of one to twelve carbon carbon atoms or —$NRR_3$ wherein
R is hydrogen or lower alkyl and
$R_3$ is hydrogen, alkyl of one to twelve carbon atoms, lower fluoroalkyl, cycloalkyl, phenyl or benzyl;
$R_2$ is hydrogen, alkyl of one to twelve carbon atoms, lower fluoroalkyl, cycloalkyl, phenyl or benzyl
$R_7$ is lower alkyl or hydrogen, provided that $R_7$ is not hydrogen when
A is H, B is a bond and x is 0; and R₈ is hydrogen, lower alkyl or lower fluoroalkyl.

2. The compound of claim 1 wherein in formula (I) wherein
A is hydrogen,
B is a bond,
x is an integer of 0 to 2,
y is 0,
I is a bond and
J is NH₂.

3. The compound of claim 2 wherein in formula (I)
C is Gly,
D is His,
E is Ser,
F is Val, and
G is Ala or Val.

4. The compound of claim 3 wherein in formula (I) G is Val and x is 0, namely

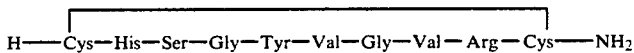

or the reduced form thereof.

5. The compound of claim 1 wherein in formula (I)
A is acyl of one to twelve carbon atoms, benzoyl, 3-(4-hydroxyphenyl)propionyl- or 3-(3,5-diiodo-4-hydroxyphenyl)propionyl;
B is a bond,
x is an integer of zero to 5,
y is 0,
I is a bond and
J is NH₂.

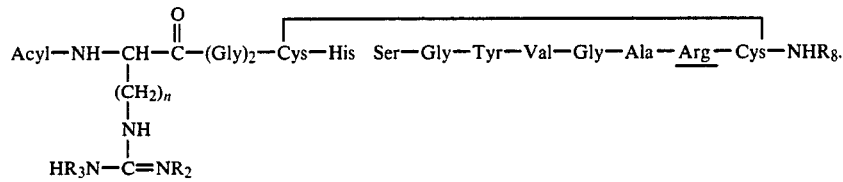

6. The compound of claim 5 wherein in formula (1)
D is His,
E is Ser,
F is Val,
G is Ala or Val and
x is 0.

7. The compound of claim 6 wherein in formula (I) A is 3-(3,5-diiodo-4-hydroxyphenyl)-propionyl or 3-(4-hydroxyphenyl)-propionyl.

8. The compound of claim 1 wherein in formula (I)
A is hydrogen or acyl of one to twelve carbon atoms,
B is the radical of formula (II) wherein R₁ is NRR₃,
C is Gly and
x is an integer of one to five.

9. The compound of claim 8 wherein in formula (II)
R is hydrogen,
R₂ is alkyl or fluoroalkyl of one to twelve carbon atoms or lower fluoroalkyl and R₃ is hydrogen or alkyl of one to twelve carbon atoms.

10. The compound o claim 9 wherein in formula (I)
y is an integer of two to five,
I is a radical of formula (II) wherein R₁ is NRR₃ and
J is NHR₈.

11. The compound of claim 9 wherein in formula (I)
x is 2,
y is zero and
I is a bond.

12. The compound of claim 11 wherein in formula (I)
D is His,
E is Ser,
F is Val and
G is Val or Ala.

13. The compound of claim 12 wherein in formula (I) G is Val.

14. The compound of claim 13 wherein in formula (I)
A is acyl of one to twelve carbons,
B is L-Deh or D-Deh and
J is NHR₈ wherein R₈ is H or CH₂CH₃.

15. The compound of claim 12 wherein in formula (I) G is Ala.

16. The compound of claim 15 wherein in formula (I)
A is acyl of one to twelve carbon atoms, and
J is —NHR₈ where R₈ is hydrogen or lower alkyl, namely

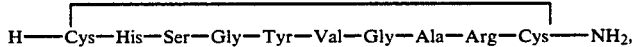

17. The compound of claim 16 wherein in formula (I) R₃ and R₂ are both lower alkyl or lower fluoroalkyl.

18. The compound of claim 17 wherein in formula (I) R₂ and R₃ are both ethyl.

19. The compound of claim 12 wherein in formula (I) J is OR₇ and R₇ is lower alkyl.

20. The compound of claim 11 wherein in formula (I)
D is Val,
E is Val or Ile,
F is Ser or Ile and
G if Asp or Glu.

21. A pharmaceutical composition which comprises a compound of claim 1 in admixture with a pharmaceutically acceptable excipient.

22. The compound which is:

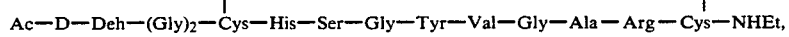

or a reduced form thereof.

23. The compound which is:

24. The compound which is:

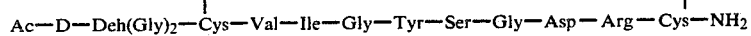

or a reduced form thereof.

25. The compound which is:

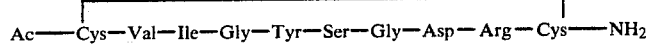

or a reduced form thereof.

26. The compound which is:

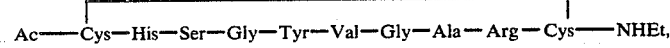

or a reduced form thereof.

27. The compound which is:

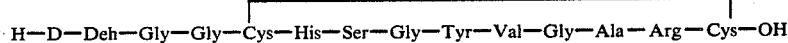

or a reduced form thereof.

28. The compound which is:

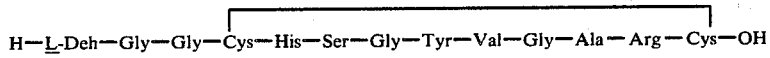

or a reduced form thereof.

29. The compound which is:

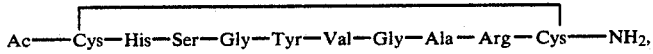

or a reduced form thereof.

30. The compound which is:

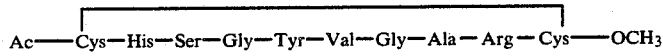

or a reduced form thereof.

31. A compound selected from the group consisting of:

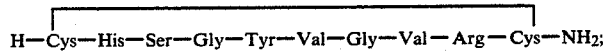

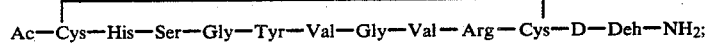

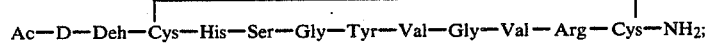

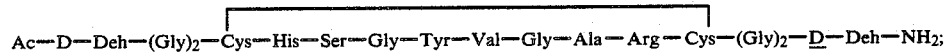

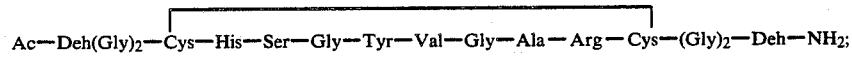

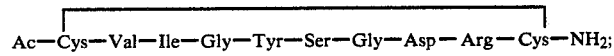

Ac—Cys—His—Ser—Gly—Tyr—Val—Gly—Val—Arg—Cys—NHEt;

Ac—Cys—Val—Val—Gly—Tyr—Ile—Gly—Glu—Arg—Cys—NHEt;

H—Gly—Cys—His—Ser—Gly—Tyr—Val—Gly—Ala—Arg—Cys—NHEt;

H—D—Deh—(Gly)$_2$—Cys—His—Ser—Gly—Tyr—Val—Gly—Ala—Arg—Cys—NHet;

Ac—Cys—His—Ser—Gly—Tyr—Val—Gly—Val—Arg—Cys—NH$_2$;

Ac—Cys—His—Ser—Gly—Tyr—Val—Gly—Val—Arg—Cys—D—Deh—NH$_2$; and

Ac—Cys—His—Ser—Gly—Tyr—Val—Gly—Val—Arg—Cys—OCH$_3$, or a reduced form of any of the above.

32. A compound represented by the formula $$A-B-C- \quad (I)$$

$$-Cys-D-E-Gly-Tyr-F-Gly-G-Arg-Cys-$$

$$-H-I-J,$$

a reduced form of said compound or a pharmaceutically acceptable salt of said compound, wherein A is hydrogen or acyl of one to twelve carbon atoms;
B is a bond or a radical of the formula $$\begin{array}{c}-HN-CH-CO-\\ | \\ (CH_2)_n \\ | \\ NH \\ | \\ R_1-C=NR_2;\end{array} \quad (II)$$

C is (Gly)$_x$;
D is Val or His;
E is Ser, Ile or Val;
F is Val, Ser or Ile;
G is Val, Ala, Asp or Glu;
H is (Gly)$_y$;
I is a bond or a radical represented by formula (II), but independent thereof; and
J is OR$_7$ or NHR$_8$;
wherein for B, C, H, I and J
n is an integer of two to five; each of x and y is independently an integer of zero to two;
R$_1$ is —NRR$_3$ wherein
R is hydrogen or lower alkyl and
R$_3$ is hydrogen, alkyl of one to twelve carbon atoms, lower fluoroalkyl, or cycloalkyl;
R$_2$ is hydrogen, alkyl of one to twelve carbon atoms, lower fluoroalkyl, cycloalkyl, phenyl or benzyl;
R$_7$ is lower alkyl or hydrogen, provided that R$_7$ is not hydrogen when A is H, B is a bond and x is 0; and
R$_8$ is hydrogen, lower alkyl or lower fluoroalkyl.

33. The compound of claim 32 wherein A is acyl of one to twelve carbon atoms and R$_7$ is lower alkyl.

* * * * *